United States Patent
Risch et al.

(10) Patent No.: US 12,145,788 B2
(45) Date of Patent: Nov. 19, 2024

(54) ABSORBER DEVICE

(71) Applicant: BIOTRONIK AG, Buelach (CH)

(72) Inventors: Fabian Risch, Doerflingen (CH); Tobias Schaefer, Blumberg-Fuetzen (DE)

(73) Assignee: BIOTRONIK AG, Buelach (CH)

( * ) Notice: Subject to any disclaimer, the term of this patent is extended or adjusted under 35 U.S.C. 154(b) by 156 days.

(21) Appl. No.: 17/910,136

(22) PCT Filed: Jan. 29, 2021

(86) PCT No.: PCT/EP2021/052061
§ 371 (c)(1),
(2) Date: Sep. 8, 2022

(87) PCT Pub. No.: WO2021/190807
PCT Pub. Date: Sep. 30, 2021

(65) Prior Publication Data
US 2023/0102707 A1   Mar. 30, 2023

(30) Foreign Application Priority Data
Mar. 23, 2020   (EP) .................................. 20164758

(51) Int. Cl.
*B65D 81/26*   (2006.01)
*A61M 25/00*   (2006.01)

(52) U.S. Cl.
CPC ......... *B65D 81/266* (2013.01); *A61M 25/002* (2013.01)

(58) Field of Classification Search
CPC .... B65D 81/266; B65D 81/268; B65D 81/26; A61M 25/002

USPC .................................................. 206/204, 222
See application file for complete search history.

(56) References Cited

U.S. PATENT DOCUMENTS

| | | | |
|---|---|---|---|
| 10,359,144 B2 | 7/2019 | Yamashita | |
| 2010/0154822 A1* | 6/2010 | Reed, Jr. | .................. A47L 13/12 |
| | | | 15/229.11 |
| 2020/0268603 A1* | 8/2020 | Kibele | .................... A61J 1/035 |

FOREIGN PATENT DOCUMENTS

| | | | |
|---|---|---|---|
| EP | 1903271 A1 | 3/2008 | |
| EP | 3315845 A1 * | 5/2018 | ............... B22C 9/00 |
| JP | H0398871 A | 4/1991 | |
| JP | 2012188126 A | 10/2012 | |
| KR | 20040060914 A * | 7/2004 | |

(Continued)

OTHER PUBLICATIONS

International Search Report from the corresponding International Patent Application No. PCT/EP2021/052061, dated Apr. 16, 2021.

*Primary Examiner* — Rafael A Ortiz
(74) *Attorney, Agent, or Firm* — Greer, Burns & Crain, Ltd.; Steven P. Fallon

(57) ABSTRACT

An absorber device for absorbing a fluid residing in an a package inner space. The absorber device includes an absorber arranged in the inner space of a container and a movable penetration device. The penetration device is configured to be moved from a first position to a second position. In the first position, the penetration device is positioned in the inner space of the container. In the second position, the penetration device is configured to penetrate a container contact section and a wall of the package. The absorber in the inner space of the container is thereby fluidically connected to the inner space of the package in the second position.

16 Claims, 5 Drawing Sheets

(56) References Cited

FOREIGN PATENT DOCUMENTS

WO         2016006186 A1    1/2016
WO   WO-2017202589 A1 * 11/2017   ........... A61F 2/0095

* cited by examiner

ABSORBER DEVICE

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2021/05206, which was filed Jan. 29, 2021, which application claimed priority from European Application Serial Number 20164758.3, which was filed Mar. 23, 2020.

FIELD OF THE INVENTION

A field of the invention is packaging, particularly packaging of medical devices. Devices of the invention can be used for absorbing a fluid residing in a package of a medical device, as a packaging system and used generally as part of a method to absorb a fluid residing in a package.

BACKGROUND

The effect of a drug dispensed by a medical device such as a drug-eluting stent can be reduced by the reaction of the drug with moisture and oxygen. To ensure long-term efficiency of the medical device, gases need to be removed from the surrounding environment of the medical device. However, during the production process, gases are part of the surrounding environment. In particular, gases are a mandatory part of the environment during the sterilisation process. For example, the sterilisation can be performed by exposing the medical device to ethylene oxide.

To remove a gas, an absorber component can be used. The absorber component can be applied after the sterilisation process, since otherwise the absorber component would become saturated during the production process.

An existing solution uses standardised absorber components with use of two separate pouches. With the use of two separate pouches, there is an inner gas-permeable pouch and an outer gas-permeable pouch. The product, in particular the medical device, is packaged and sterilised in the inner gas-permeable pouch. The outer pouch is filled with the packaged and sterilised product and the absorber component and is then closed. When using such a two-pouch-system, the user has to open two pouches, such that it is not user-friendly. Since two pouches are needed, greater material costs are incur and more waste is produced. The packing process is more complex, thus incurring greater process costs. Because of the larger packing volumes, a larger storage volume is necessary, which can also incur the costs. Moreover, the outer surface of the inner pouch is not sterile.

A further existing solution uses standardised absorber components with use of a specific pouch design, wherein the pouch has two chambers, in particular a product chamber and an absorber chamber, which make it possible to add an absorber after sterilisation without opening the product chamber. The gas exchange between absorber chamber and product chamber occurs via a porous membrane. Packaging of this type are known for example from U.S. Pat. No. 8,297,439. B2. A disadvantage of a pouch having two chambers is constituted generally by the additional material costs caused by a relatively complex pouch design with additional material layers. There is also more waste produced by the additional packaging material.

Another existing solution is disclosed in WO 2017/202 589 A1. The described packaging comprises a container arranged in the interior space of the packaging. The absorber is arranged in the container. When an object is positioned in the interior space of the packaging and the packaging is closed, the container opens such that the absorber can absorb gas from the interior space of the packaging.

SUMMARY OF THE INVENTION

A preferred absorber device for absorbing a fluid enclosed by a package includes a container having a wall enclosing a container inner space. The wall includes container contact section that is configured to be penetrated. An absorber is arranged in the container inner space. A movable penetration device is configured to be moved from a first position to a second position. In the first position, the penetration device is positioned in the container inner space and in the second position is positioned to penetrate the contact section and a package arranged against the container contact section such that the container inner space can be fluidically connected to a package inner space to fluidly connect the absorber to the package inner space.

BRIEF DESCRIPTION OF THE DRAWINGS

In the following, further features, advantages and embodiments of the present invention are explained with reference to the Figures, wherein.

DETAILED DESCRIPTION OF THE PREFERRED EMBODIMENTS

Figure 1A:
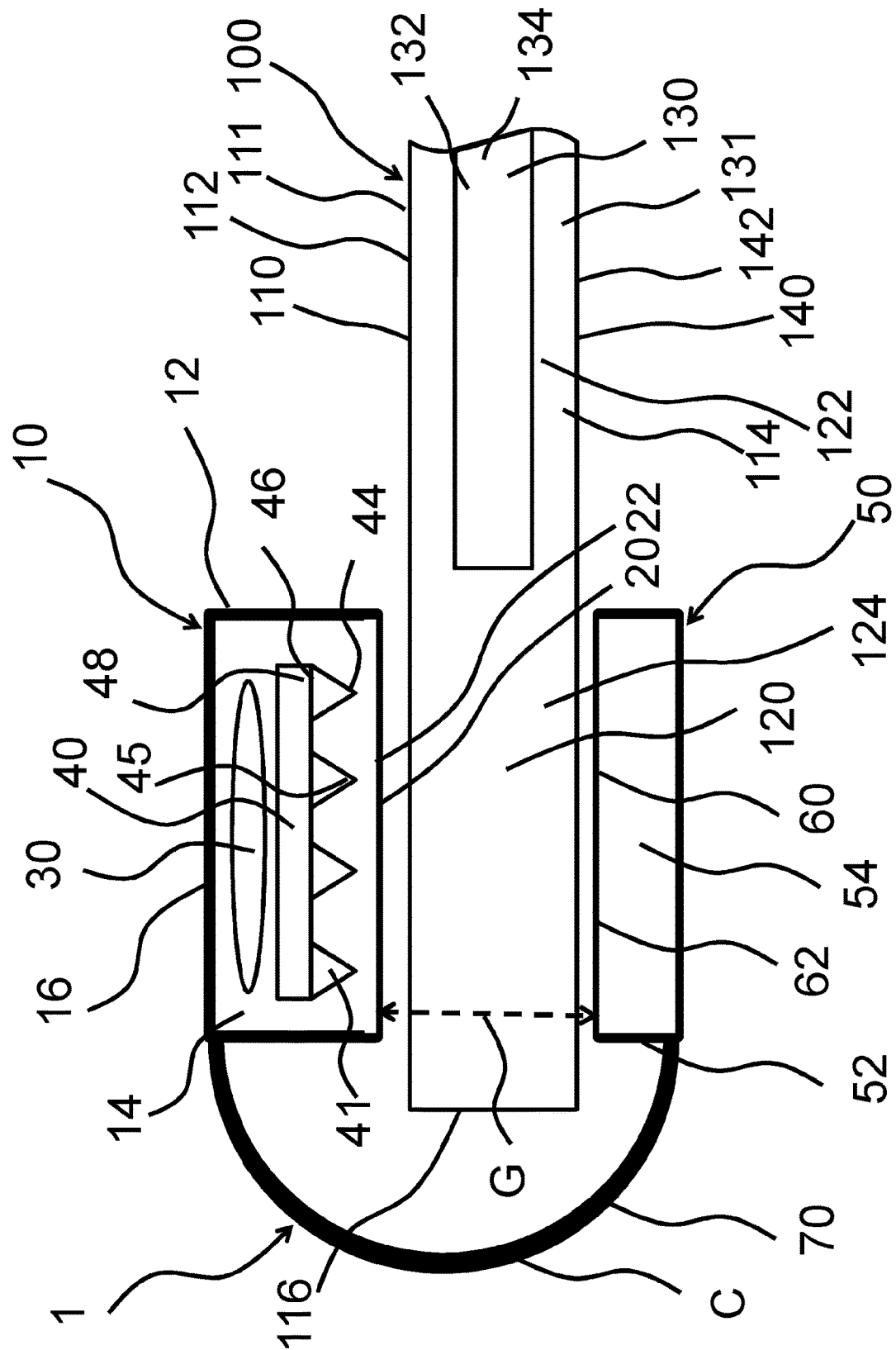
FIG. 1A shows a schematic cross section view of an absorber device, wherein the penetration device is in the first position, and the package is positioned between the container and the counter member.

A first aspect of the invention is related to an absorber device for absorbing a fluid residing in an inner space enclosed by a package of a medical device, the package including a wall enclosing the inner space of the package. According to the invention, the absorber device includes a container, wherein the container includes a wall enclosing an inner space of the container, wherein the wall includes a contact section, wherein the contact section is configured to be mechanically penetrated (e.g. pierced). The absorber device includes an absorber arranged in the inner space of the container, and a movable penetration device. The penetration device is configured to be moved from a first position to a second position, wherein in the first position, the penetration device is positioned in the inner space of the container, and wherein in the second position, the penetration device is configured to penetrate the contact section and the wall of the package, when the contact section is arranged on an outer surface of the wall of the package, such that the inner space of the container is fluidically connected to the inner space of the package to thereby allow fluid from the inner space of the package to pass to the inner space of the container and be absorbed by the absorber.

The fluid can be a gas, in particular air. It can include oxygen ($O_2$) and/or water ($H_2O$).

The package can be configured to be closed. In particular, the package can be closed after a medical device has been positioned in the inner space of the package (enclosed by the wall of the package).

The medical device can be sterilised in the inner space of the package. The medical device can be sterilised by ethylene oxide, particularly gaseous ethylene oxide. The package can generate a sterile barrier.

The medical device can be a stent, particularly a drug-eluting stent. The medical device can be a catheter such as a balloon catheter. The medical device can be one of a biosensor, a dialysis unit, a drug delivery system, an electrode, a vascular cuff, a pacemaker, a cardiac pacemaker, a defibrillator, a cardioverter, a brain pacemaker, a neuroprosthetic, electrodes/electronics for artificial limbs, a nerve stimulator, a barostimulator, a kidney pacemaker, a duodenal pacemaker, a heart implant, a tumour-monitoring implant, an artificial heart, an artificial heart valve primarily with artificial or natural tissue, a shunt, a brain shunt, a hydrocephalus implant, an occluder, natural tissue, preferably dried natural tissue, a telemetry unit, a receiving unit, a transmitting unit, a pressure sensor, an organ replacement, an energy harvesting implant, a bio fuel cell, a catheter, a cochlear implant, a retina implant, a dental implant, an artificial implantable lens system, an implant for joint replacement, and a vascular prosthesis; in particular if these implants include an antibacterial coating or a coating delivering an active substance. Contact lenses and bone implants, such as nails or screws, can also be packaged in the inner space of the package.

However, the package can also be used in other fields apart from the medical engineering, for example in the food or pharmaceutical industries.

The container of the absorber device can include a wall. According to the invention, the wall includes a penetrable contact section. The wall can include a back wall opposing the contact section. The wall can include a side wall connecting the back wall and the contact section. In an embodiment, the wall of the container is impervious to fluids. In an embodiment, the wall of the container is gas-tight. In other words, the wall of the container can be impervious to gases.

The absorber can be arranged in the inner space of the container. In an embodiment, the absorber is packed gas-tightly in the inner space of the container.

The container can be positioned on the package. The container can be arranged such with respect to the package that the contact section is arranged on an outer surface of the wall of the package. The contact section can be pressed against the outer surface of the wall of the package. The contact section can be connected to the outer surface of the wall of the package (e.g. by way of a substance-to-substance bond).

The contact section is penetrable. This means that the contact section can be configured such that a pointed item can pass through it to form at least one through-hole into the contact section. According to an embodiment, the contact section is configured to be penetrated (e.g. pierced) by the penetration device of the absorber device, when the penetration device is in the second position.

In the first position, the penetration device can be arranged in the inner space of the container. In particular, the contact section can be closed, when the penetration device is in the first position.

In the second position, the penetration device penetrates the contact section. In particular, at least a part of the penetration device can pass through the contact section thereby destroying a corresponding portion of the contact section. When passing through the contact section, the penetration device can generate a through-opening in the contact section. In the second position, at least a first part of the penetration device can be positioned outside of the inner space of the container. In an embodiment, a second part of the penetration device is positioned in the inner space of the container, when the penetration device is in the second position.

When the contact section is arranged on an outer surface of the wall of the package, the penetration device can penetrate the contact section and the wall of the package, in particular, an access section of the wall of the package at which the contact section is arranged. The penetration device can generate a through-opening in the contact section and in the wall of the package, in particular in the access section.

By penetration of the contact section and the wall of the package arranged on the contact section, the inner space of the container is fluidically connected to the inner space of the package. The inner space of the container and the inner space of the package can be fluidically connected via the through-opening in the contact section and the access section.

When the inner space of the container and the inner space of the package are fluidically connected, the fluid from the inner space of the package can pass to the inner space of the container. The fluid can pass via the through-opening in the contact section and the access section.

According to the invention, the penetration device is movable. In particular, the penetration device is movable from the first position to the second position. The penetration device can be moved from the first position to the second position along a transfer direction. The transfer direction can extend perpendicular to the contact section.

The absorber device can be configured such that the absorber device is compatible with a commercially available package. Advantageously, the absorber device is applicable with a well-established package, i.e. commercially available package. This means that an existing package can be used in combination with the absorber device. No additional costs occur due to the necessity of buying a specific (expensive) package in order to be compatible with the absorber device according to the invention because existing package can be used.

The waste usually accumulated can be reduced, because no further packaging chambers and/or pouches have to be provided to absorb an inadvertent fluid from a package.

A further advantage of the absorber device according to an embodiment is that the absorber is gas-tightly packed in the inner space of the container. Hence, the absorber is shielded. In particular, the container (the wall of the container) can protect the absorber from the surrounding environment, which might consume or even saturate the absorber, such that the absorber could not absorb the fluid from the inner space of the package.

The protection of the absorber by the container advantageously simplifies the handling of the absorber during the production process. Absorber arranged in the absorber device according to the invention can easily be stored.

In an embodiment, the contact section includes an outer surface, wherein the outer surface of the contact section is capable of connecting, in particular in a gas-tight manner, to the wall of the packaging. In one embodiment the outer surface of the contact section is adhesive.

According to an embodiment, the outer surface of the contact section can be coated with an adhesive.

In an embodiment, the outer surface of the contact section is configured such that the outer surface of the contact section sticks together with the wall of the packaging, when the contact section is arranged on the wall of the packaging. In particular, the outer surface of the contact section can be configured to adhere to the outer surface of the wall of the package, when the contact section is arranged on the wall of the package. The contact section can be attached firmly to the wall of the packing via the adhesive outer surface of the contact section, such that the contact section can be positively connected to the outer surface of the wall of the package.

The wall of the package contact section and the contact section adhered to the wall of the package can form a joint sterile barrier.

Using the adhesive outer surface of the contact section the contact section can be easily connected, particularly positively connected, to the outer surface of the wall of the package. The joint sterile barrier can be easily generated by sticking together the outer surface of the contact section and the outer surface of the wall of the package. In one embodiment the outer surface of the contact section may be configured to have a concave form facilitating the onset of the contact section at the summit of the concave surface and a subsequent airtight connection with the counterpart from the summit downwards.

Also other ways of connecting the contact section to the wall of the packaging are conceivable besides a contacting based on adhesives. One option is based on chemical or physical activation of both surfaces, reversible or permanent, the one of the contact section and the other on the wall of the packaging. Also, positive or non-positive air tight connection can be applied. In addition a sealing can be implemented.

According to a further embodiment, the contact section includes or consists of aluminium or an aluminium alloy. In an embodiment, the contact section includes or consists of a foil including or consisting of aluminium or an aluminium alloy. Also, the contact section includes or consists of gas-tight polymers, for example ethylene-vinyl alcohol copolymer (EVOH) and polyvinylidene chloride (PVdC), glass or glass-based materials or other suitable metals or metal alloys.

The contact section can include a plastic-reinforced aluminium alloy. In an embodiment, the contact section consists of a plastic-reinforced aluminium alloy. According to an embodiment, the contact section consists of a plastic-reinforced foil including an aluminium alloy. The contact section can include a plastic-reinforced foil including an aluminium alloy.

The contact section can be bond to the wall, particularly the side wall, of the container. The contact section can be welded to the side wall of the container.

A foil including or consisting of aluminium or the aluminium alloy can be easily penetrated by the penetration device. A foil including or consisting of aluminium or an aluminum alloy that is reinforced by plastic can increase the protection of the absorber by the container because it can be more stable such that it protects better against an inadvertent penetration of the contact section e.g. during storage of the absorber device.

The wall of the container can include or consist of aluminium or an aluminium alloy, glass or plastic, in particular plastic impervious to fluids, in particular gas-tight plastic. In an embodiment, the back wall includes gas-tight plastic. The back wall can consist of plastic, particularly gas-tight plastic. According to an embodiment, the back wall includes aluminium or an aluminium alloy. In a further embodiment, the back wall consists of aluminium or the aluminium alloy. The side wall can include aluminium, an aluminium alloy, glass or a gas-tight plastic. The side wall can consist of aluminium, aluminium alloy, glass or a gas-tight plastic.

According to an embodiment, the back wall is configured to be depressible. The back wall can be configured to be pressed into the inner space of the container, in particular, by a force acting with a vector component along the transfer direction of the penetration device.

In an embodiment, the penetration device includes at least one tapered element.

According to an embodiment the tapered element includes a pointed end. The tapered element can form a tip for penetration. The tapered element can include a tip for penetration. The pointed end can be the tip for penetration. The tapered element can be a needle. In an embodiment the tapered element is a spike. In another embodiment the tapered element is a blade, in particular configured to cut the contact section and the wall of the packaging along a cutting line.

The tapered element can be configured to penetrate the contact section, when the penetration device is in the second position. In an embodiment, the tapered element is configured to penetrate the contact section and the wall of the package, when the contact section and the wall of the package form the joint sterile barrier and the penetration device is in the second position.

In an embodiment, the penetration device includes a plurality of tapered elements.

In a further embodiment the absorber includes or consists of an oxygen absorber. According to an embodiment, the absorber includes or consists of a moisture absorber.

In an embodiment, the absorber is a standard absorber which is commercially available. The absorber can be the PharmaKeep KD-20 absorber by MGC.

In an embodiment the inner space of the container is sterile.

According to an embodiment, the inner space of the container and the absorber arranged in the inner space of the container are sterile. The inner space of the container and the perforation device can be sterile. In an embodiment, the inner space of the container, the perforation device and the absorber are sterile.

The sterilisation of the inner space of the container and the absorber can be obtained by radiation. In an embodiment, the inner space of the container is sterile upon alpha radiation. In a further embodiment, the inner space of the container is sterile upon beta radiation. The inner space of the container can be sterile upon gamma radiation.

The absorber can be positioned in the inner space of the container during the sterilisation by radiation. Upon radiation the absorber can remain its capability to absorb inadvertent fluid.

A further embodiment is characterized in that the absorber device includes a counter member, wherein the counter member includes a further contact section facing the contact section, wherein the container and the counter member are configured to be movable towards each other to clamp the package between the container and the counter member.

In an embodiment, the container is movable towards the counter member to clamp the package between the container and the counter member. According to an embodiment, the counter member is movable towards the container to clamp the package between the container and the counter member.

The further contact section can be arranged on the wall of the package. In an embodiment, the further contact section can be arranged on the outer surface of the wall of the package.

In an alternative embodiment, the counter member is arranged in the inner space of the package. The counter member can be configured such that it can be arranged on an inner surface of the wall of the package. The inner surface of the wall of the package can face towards the inner space of the package.

The counter member can be configured to provide an abutment for the container. In particular, the counter member can constitute an abutment for the container, when the package is clamped between the container and the counter member.

In an embodiment, the further contact section is configured to be penetrated.

In particular, the further contact section can be configured to be penetrated by the penetration device. The further contact section can be configured to be penetrated by the tapered element of the penetration device.

The further contact section can include or consists of aluminium alloy. According to an embodiment, the further contact section includes or consists of a foil including an aluminium alloy. The further contact section can include or consist of a foil consisting of aluminium alloy.

According to an embodiment, the further contact section includes a plastic-reinforced aluminium alloy, in particular a respective foil. The further contact section can consist of a plastic-reinforced aluminium alloy, in particular a respective foil.

According to an embodiment, the further contact section includes an outer surface opposing the outer surface of the contact section, wherein the outer surface of the further contact section is adhesive.

According to an embodiment, the outer surface of the further contact section can be coated with an adhesive.

In an embodiment, the outer surface of the further contact section is configured such that the outer surface of the further contact section sticks to the wall of the packaging, when the further contact section is arranged on the wall of the packaging. The further contact section can be attached firmly to the wall of the packing via the adhesive outer surface of the further contact section.

In an embodiment, the further contact section is arranged distant to the contact section such that the package is positionable between the contact section and the further contact section, when the penetration device is in the first position.

According to an embodiment, the absorber device is configured such that the contact section extends parallel to the further contact section. The contact section and the further contact section can be separated by a gap. The package can be positioned in the gap, in particular when the penetration device is in the first position. The gap can be configured such that the package is insertable in the gap.

In a further embodiment, when the penetration device is in the second position, the penetration device penetrates the contact section, the wall of the package and the further contact section, when the contact section is arranged on the wall of the package and the further contact section is arranged on the wall of the package.

The contact section can be arranged on the outer surface of the wall of the package. In particular, the outer surface of the contact section can be arranged on the outer surface of the wall of the package. The outer surface of the contact section can be arranged on the access section of the wall of the package.

The further contact section can be arranged on the outer surface of the wall of the package. In particular, the outer surface of the further contact section can be arranged on the outer surface of the wall of the package. The outer surface of the further contact section can be arranged on a further access section of the wall of the package. According to an embodiment, the access section opposes the further access section.

When the package is clamped between the container and the counter member and the penetration device is in the second position, the penetration device can penetrate the contact section, the wall of the package and the further contact section.

Clamping the package between the contact section and the further contact section can generate the joint sterile barrier and the further joint sterile barrier.

When the joint sterile barrier and the further joint sterile barrier are generated and the penetration device is in the second position, the penetration device can penetrate the contact section, the wall of the package and the further contact section. This means that the penetration device, particularly the tapered element, can penetrate the joint sterile barrier and the further joint sterile barrier, when the penetration device is in the second position.

The counter member can include an inner space. According to an embodiment, when the penetration device is in the second position and the contact section is arranged on the wall of the package and the further contact section is arranged on the wall of the package, such that the penetration device penetrates the contact section, the wall of the package and the further contact section, the inner space of the container can be fluidically connected to the inner space of the package and the inner space of the counter member.

According to an embodiment, the container and the counter member are connected to one another.

The container and the counter member can be connected such that the contact section of the container and the further contact section of the counter member extend parallel to each other.

In an embodiment, the counter member and the container are configured and connected such that the contact section and the further contact section face each other. The container and the counter member can be connected such that the contact section and the further contact section are distant to each other when the penetration device is in its first position. In an embodiment, the container and the counter member are movably connected. In particular, the container and the counter member can be connected such that they are movable towards each other.

According to an embodiment, the container is connected to the counter member via a connector.

A second aspect of the invention is related to a packaging system preferably for a medical device, including a package, wherein the package includes a wall enclosing an inner space of the package, wherein the package is configured such that the object to be packed, preferably a medical device, is arrangeable in the inner space of the package, and an absorber device, in particular the absorber device according to the invention.

In an embodiment, a sterile medical device is arrangeable in the inner space of the package.

The packaging system according to the invention can also be used in the context of packing of objects other than medical devices, for example food or pharmaceuticals. The package of the packaging system can be configured such that the particular object can be arrangeable in the inner space of the package.

According to an embodiment, the packaging system includes a counter member arranged in the inner space of the package, wherein the counter member and the container are arranged and configured such that the container is movable towards the counter member to clamp the wall of the package between the container and the counter member.

In an embodiment, the counter member is positioned in the inner space of the package.

According to an embodiment, the counter member is arrangeable on an inner surface of the wall of the package. The inner surface of the wall of the package can be directed towards the inner space of the package.

A further aspect of the invention is related to a method to absorb a fluid residing in an inner space of a package, for instance of a medical device, including the steps of:
providing the package, wherein the package includes a wall enclosing an inner space of the package,
providing an absorber device, wherein the absorber device includes a container including a wall enclosing an inner space of the container, wherein the wall includes a contact section configured to be penetrated, an absorber arranged in the inner space of the container, and a movable penetration device, wherein the penetration device is configured to be moved from a first position to a second position, in particular the absorber device according to the invention, wherein the penetration device is in the first position,
arranging the package and the absorber device such with respect to each other that the contact section of the container is arranged on an outer surface of the wall of the package,
moving the penetration device from the first position to the second position such that the penetration device penetrates the contact section and the wall of the package to thereby allowing the fluid to pass from the inner space of the package to the inner space of the container and to be absorbed by the absorber.

In an embodiment, the method includes the steps of:
providing the package,
providing an absorber device, wherein the absorber device includes the container and a counter member, wherein the counter member includes a further contact section facing the contact section, wherein the container and the counter member are configured to be movable towards each other to clamp the package between the container and the counter member,
arranging the package and the absorber device such with respect to each other that the contact section is arranged on the wall of the package and the further contact section is arranged on the wall of the package, particularly clamping the package between the container and the counter member,
moving the penetration device from the first position to the second position such that the penetration device penetrates the contact section, the wall of the package and the further contact section to thereby allowing the fluid to pass from the inner space of the package to the inner space of the container and to be absorbed by the absorber.

According to a further embodiment of the method, the method includes the steps of:
providing a packaging system including a package for an object, in particular for a medical device, wherein the package includes a wall enclosing an inner space of the package, wherein the package is configured such that the object is arrangeable in the inner space of the package, and an absorber device, in particular the absorber device according to the invention, in particular a packaging system according to the invention, wherein the penetration device is in the first position,
arranging the packaging system such that the contact section of the container is arranged on an outer surface of the wall of the package,
moving the penetration device from the first position to the second position such that the penetration device penetrates the contact section and the wall of the package, such allowing the fluid to pass from the inner space of the package to the inner space of the container and to be absorbed by the absorber.

Figure 1B:
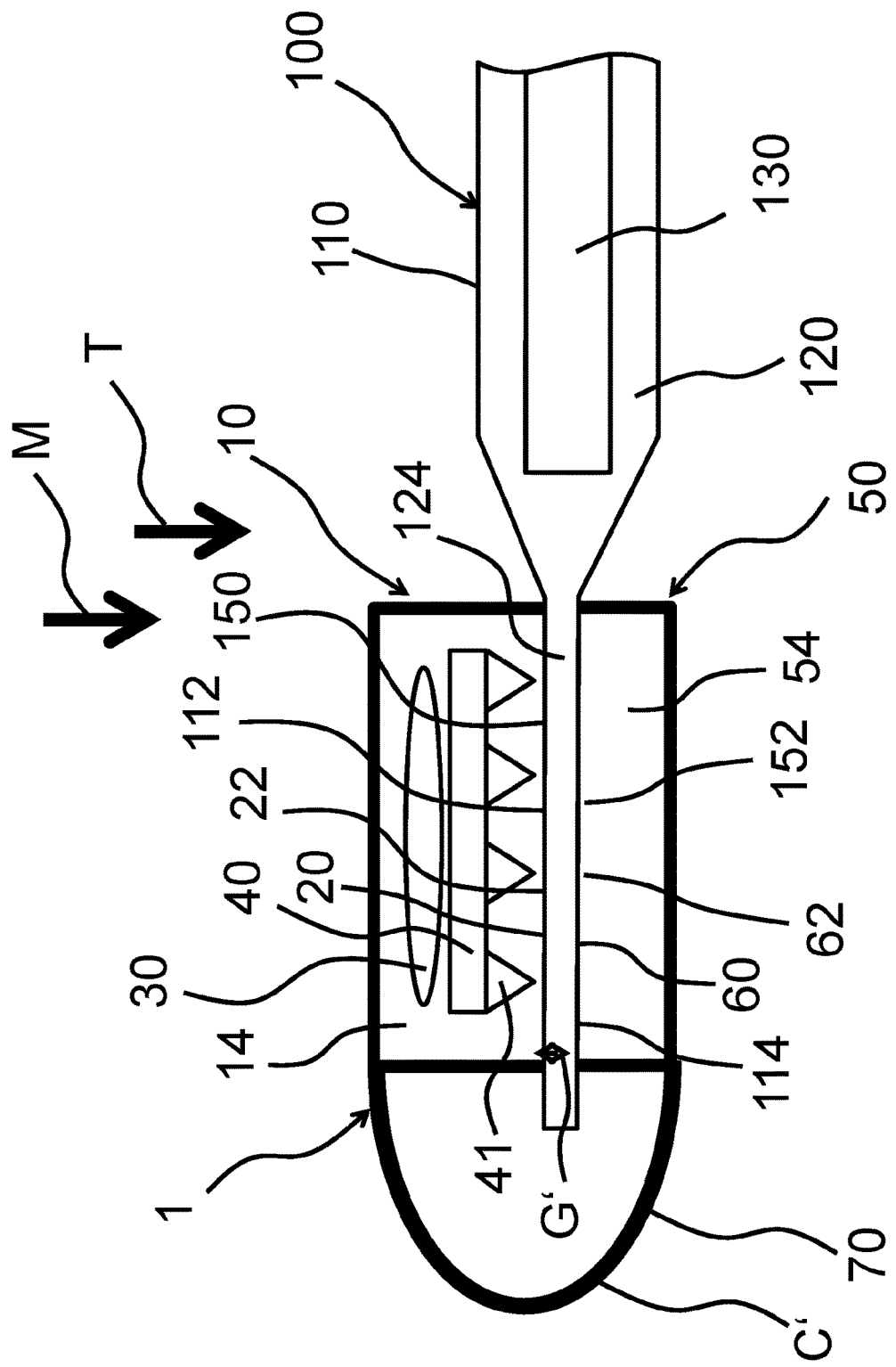
FIG. 1B shows the absorber device of FIG. 1a, wherein the penetration device is in the first position, and the contact section and the further contact section are arranged on the wall of the package.
Figure 2:
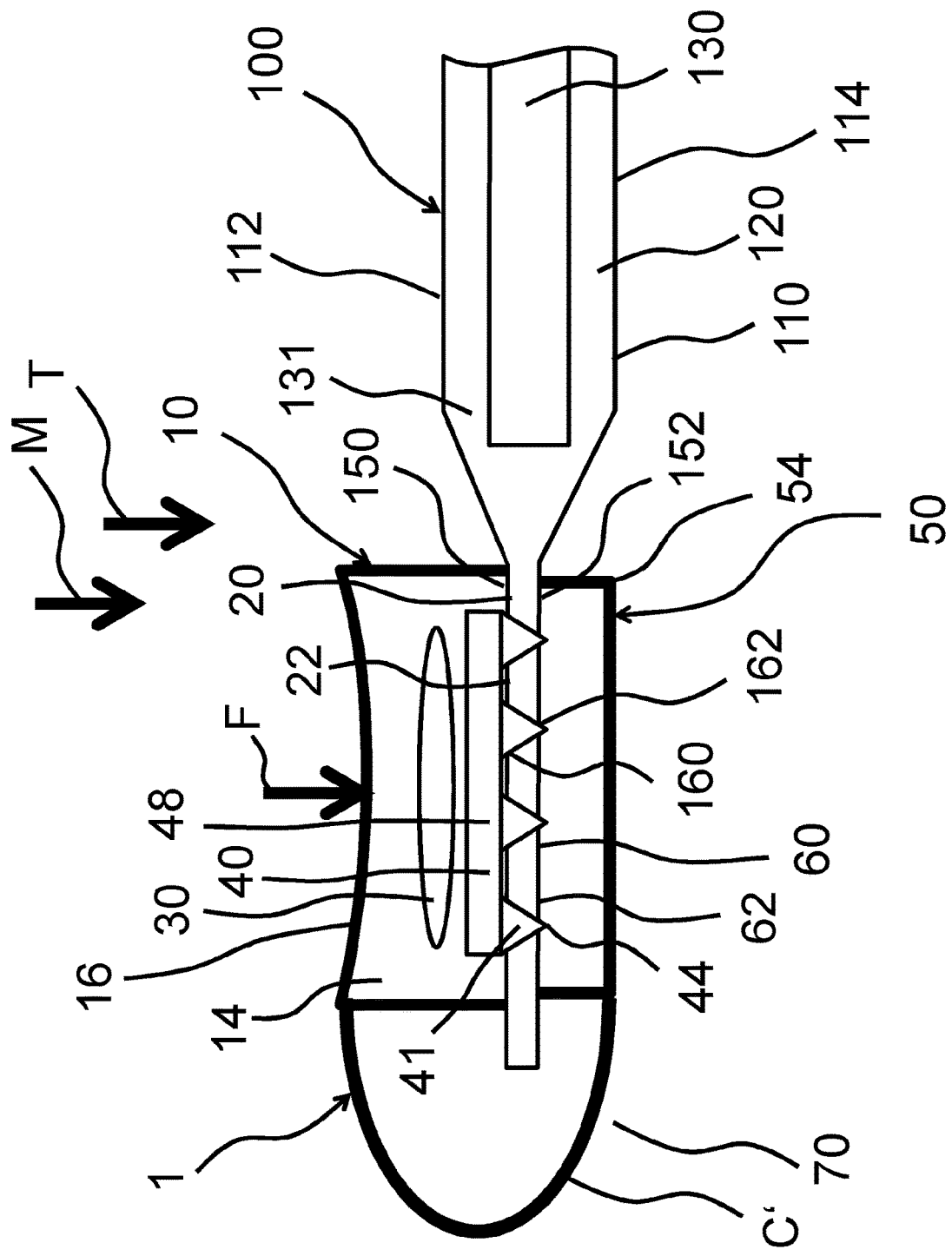
FIG. 2 shows the absorber device of FIG. 1, wherein the penetration device is in the second position.

In FIGS. 1A, 1B and 2, an embodiment of an absorber device 1 is presented. The figures further show an embodiment of a package 100. The absorber device 1 and the package 100 illustrated in FIGS. 1A-1B and FIG. 2 together form a packaging system.

The package 100 can include a wall 110 of the package 100 delimiting an inner space 120 of the package. The wall 110 of the package 100 can form a sterile barrier 111. The wall 110 can include an outer surface 140 and an opposing inner surface 142. The wall 110 of the package 100 can include a front side 116. The wall 110 can include a top side 112. The wall 100 of the package 100 can include an opposing bottom side 114.

The inner space 120 of the package 100 can include a residing portion 122. According to an embodiment, the inner space 120 of the package 100 includes an access portion 124.

An object 130 can be arranged in the inner space 120 of the package 100. In particular, the object 130 can be arranged in the residing portion 122. The wall 110 of the package 100 can enclose the object 130. In an embodiment, the object 130 is a medical device 132. The object 130 can be a catheter 134.

A fluid 131 can be arranged in the inner space 120 of the package 100. The fluid 131 can flow around the object 130 arranged in the inner space 120 of the package 100.

The absorber device 1 can include a container 10. The container 10 can include a wall 12. The wall 12 of the container 10 can include a back wall 16. The absorber device 1 can include a contact section 20, wherein the contact section 20 can include an outer surface 22. The wall 12 of the container can include the contact section 20. The contact section 20 can be positioned opposite to the back wall 16. An inner space 14 can be delimited by the wall 12 of the container 10. The outer surface 22 of the contact section 20 can face away from the inner space 14 of the container 10. The outer surface 22 of the contact section 20 can be adhesive.

A penetration device 40 can be arranged in the inner space 14 of the container 10. The penetration device 40 can include a tapered element 41, in particular a plurality of tapered elements 41. The tapered element 41 can include a pointed end 44. The tapered element can form a tip 45 for penetration. The tapered element 41 can include a base 46 opposing the pointed end 44.

In an embodiment, the respective tapered element 41 is arranged, particularly fixed, on a mounting plate 48 via its base 46. Particularly, each tapered element 41 of the plurality of tapered elements 41 is arranged on the mounting plate 48. In an embodiment, the respective tapered elements 41 point in the same direction. The pointed ends 44 of the tapered elements 41 can point in the same direction. According to an embodiment, the penetration device 40 is configured and arranged such in the inner space 14 of the container 10 that the tapered element 41 tapers towards the contact section 20, when the penetration device 40 is in the first position. In an embodiment, the penetration device 40 is configured such that the pointed end 44 of the tapered elements 41 points towards the contact section 20, when the penetration device 40 is in the first position (see FIG. 1A, FIG. 1B).

An absorber 30 can be arranged in the inner space 14 of the container 10. The absorber 30 can be positioned between the wall 12 of the container and the penetration device 40. In an embodiment, the absorber 30 is positioned between the mounting plate 48 of the penetration device 40 and the wall 12 of the container 10, in particular the back wall 16 of the container.

The absorber device 1 can include a counter member 50. The counter member 50 can include a wall 52 of the counter member 50. The wall 52 of the counter member 50 can define an inner space 54 of the counter member 50. The counter member 50 can include a further contact section 60. According to an embodiment, the further contact section 60 includes an outer surface 62.

The counter member 50 can face the container 10. In particular, the outer surface 62 of the counter member 50 can face the outer surface 22 of the contact section 20 of the container 10. In an embodiment, the outer surface 62 of the further contact section 60 runs in parallel with the outer surface 22 of the contact section 20. According to an embodiment, the outer surface 22 of the container 10 and the outer surface 62 of the counter member 50 are separated from each other by a gap G.

In an embodiment, the container 10 and the counter member 50 are connected with each other via a connector 70. The connector 70 can be curved.

The absorber device 1 can be moved from an initial position towards a contact position. The absorber device can be moved from a contact position towards a penetration position.

FIG. 1A illustrates the absorber device 1 in the initial position. In the initial position, the penetration device 40 can be in the first position. This means that the penetration device 40 can be positioned in the inner space 14 of the container 10. In the initial position, the gap G between the outer surface 22 of the contact section 20 and the outer surface 62 of the further contact section 60 can be configured such that the package 100 can be arranged in the gap G. This means that the package 100 can be positioned between the outer surface 22 of the contact section 20 and the outer surface 62 of the further contact section 60. The package 100 can be positioned such in the gap G that the top side 112 of the wall 110 of the package 100 points towards the outer surface 22 of the contact section 20 and the bottom side 114 of the wall 100 of the package 100 points towards the outer surface 62 of the further contact section 60. In the initial position, the wall 110 of the package 100 can be distant to the outer surface 22 of the container 10. The wall 110 of the package 100 can be distant to the outer surface 62 of the further contact section 60. The front side 116 of the wall 100 of the package 100 can point towards the connector 70.

The absorber device 1 can be arranged such with respect to the package 100 that the outer surface 22 is arranged above a section of the top side 112 delimiting the access portion 124 of the inner space 120 of the package 100. The absorber device 1 can be arranged such with respect to the package 100 that the outer surface 62 of the counter member 50 is arranged below a section of the bottom side 114 delimiting the access portion 124 of the inner space 120 of the package 100. The access portion 124 of the inner space 120 of the package can be arranged in the gap G.

The connector 70 can be in a relaxed state with a relaxed curvature C.

FIG. 1B illustrates the absorber device 1 in a contact position. In the contact position, the penetration device 40 is in the first position. In the contact position, the gap G' between the outer surface 22 of the contact section 20 and the outer surface 62 of the further contact section 60 can be smaller than the gap G in the initial position (compare FIG. 1A and FIG. 1B). The container 10 and the counter member 50 can be moved towards each other from the initial position towards the contact position. In particular, the container 10 can be moved from the initial position along a moving direction M towards the counter member 50, such that the absorber device 1 is in the contact position. The moving direction M can be perpendicular to the outer surface 22 of the contact section 20. The moving direction M can be perpendicular to the outer surface 62 of the further contact section 60. In an embodiment, the counter member 50 is moved towards the container 10 in a direction opposing the moving direction M.

According to an embodiment, in the contact position, the connector 70 is in a tensed state with a tensed curvature C'. The tensed curvature C' can be greater than the relaxed curvature C in the initial position (compare FIG. 1A and FIG. 1B).

In the contact position, the outer surface 22 of the contact section 20 can contact the top side 112 of the wall 110 of the package 100. In particular, the outer surface 22 of the contact section 20 of the container 10 can be positively connected with the wall 110 of the package 100, particularly with the top side 112 of the wall 110 of the package 100. In particular, the outer surface 22 of the contact section 20 of the container 10 can contact the outer surface 140 of the wall 110 of the package 100. The outer surface 62 of the further contact section 60 can contact the bottom side 114 of the wall 110 of the package 100. In particular, the outer surface 62 of the counter member 50 can be positively connected with the wall 110 of the package 100, particularly with the bottom side 114 of the wall 110 of the package 100. This means that in the contact position, the container 10 can contact the wall 110 of the package 100 via the outer surface 22 of the contact section 20. The outer surface 62 of the further contact section 60 of the counter member 50 can contact the outer surface 140 of the wall 110 of the package 100. In the contact position, the counter member 50 can contact the wall 110 of the package 100 via the outer surface 62 of the further contact section 60. In the contact position, the container 10 can contact the top side 112 of the wall 110 of the package 100 via the outer surface 22 of the contact section 20 and the counter member 50 can contact the opposing bottom side 114 of the wall 110 of the package 100 via the outer surface 62 of the further contact section 60.

In an embodiment, in the contact position, the package 100 is partly pressed together by the absorber device 1. In an embodiment, the access portion 124 of the inner space 120 of the package 100 is pressed together by the absorber device 1 in the contact position.

In an embodiment, the outer surface 22 of the contact section 20 is adhesive. In the contact position shown in FIG. 1B, the outer surface 22 of the contact section 20 can adhere to the wall 110 of the package 100, in particular to the top side 112 of the wall 110 of the package 100. The outer surface 22 of the contact section 20 and the wall 110 of the package 100 can positively connect. When the outer surface 22 of the contact section 20 is positively connected with the wall 110 of the package 100, they can form a joint sterile barrier 150.

According to an embodiment, the outer surface 62 of the further contact section 60 is adhesive. In the contact position shown in FIG. 1B, the outer surface 62 of the further contact section 60 can adhere to the wall 110 of the package 100, in particular to the bottom side 114 of the wall 110 of the package 100. The outer surface 62 of the further contact section 60 and the wall 110 of the package 100 can positively connect. When the outer surface 62 of the further contact section 60 is positively connected with the wall 110 of the package 100, they can form a further joint sterile barrier 152.

In the contact position, the penetration device 40 can be moved along a transfer direction T toward the counter member 50. The movement of the penetration device 40 along the transfer direction T can transfer the absorber device 1 from the contact position to a penetrating position. FIG. 2 illustrates an embodiment of the absorber device 1 in a penetrating position.

In an embodiment, a force F is exerted on the back wall 16 of the container 10 such that the back wall 16 is pressed in the inner space 14 of the container 10. The force F can be directed along the moving direction M. The force F can be directed along the transfer direction T. The transfer direction T can be directed parallel to the moving direction M. The transfer direction T can be directed perpendicular to the contact section 20 of the container 10. Pressing the back wall 16 in the inner space 14 of the container 10 can move (particularly push) the penetration device 40 along the transfer direction T towards the counter member 50.

Pushing of the back wall 16 of the container 10 into the inner space 14 of the container 10 can move the absorber 30 along the transfer direction T.

In the penetration position, the penetration device 40 can penetrate the contact section 20. In the penetration position, the penetration device 40 can penetrate the outer surface 22 of the contact section 20. In the penetration position, the penetration device 40 can penetrate the wall 110 of the package 100. In particular, in the penetration position, the penetration device 40 can penetrate the top side 112 of the wall 110 of the package 100. According to an embodiment, the penetration device 40 penetrates the joint sterile barrier 150. In particular, the tapered element 41 of the penetration device 40 can penetrate the contact section 20. The tapered element 41 can penetrate the wall 110 of the package 100. According to an embodiment, in the penetration position, the tapered element 41 can penetrate the joint sterile barrier 150.

In an embodiment, the penetration device 40, particularly the tapered element 41, forms a through-opening 160 in the joint sterile barrier 150, when penetrating the joint sterile barrier 150. In an embodiment, a pointed end 44 of the tapered element 41 can stick into the inner space 120 of the package 100 (see also FIG. 3).

By penetrating the contact section 20 and the top side 112 of the wall 110 of the package 100, the inner space 14 of the container 10 can be connected, particularly fluidically connected, with the inner space 120 of the package 100. When the inner space 120 of the package 100 and the inner space 14 of the container 10 are connected, the fluid 131 from the inner space 120 of the package 100 can pass to the inner space 14 of the container 10. In the inner space 14 of the container 10, the fluid 131 can contact the absorber 30.

According to an embodiment, in the penetration position, the penetration device 40 penetrates the bottom side 114 of the wall 110 of the package 100. The penetration device 40 can penetrate the further contact section 60. In particular, in the penetration position, the penetration device 40 can penetrate the further joint sterile barrier 152. In an embodiment, the tapered element 41 can penetrate the bottom side 114 of the wall 110 of the package 100. The tapered element 41 can penetrate the further contact section 60 of the counter member 50. In particular, the tapered element 41 can penetrate the further joint sterile barrier 152. In an embodiment, the pointed end 44 of the tapered element 41 of the penetration device 40 can stick into the inner space 54 of the counter member 50.

The penetration of the bottom side 114 of the wall 110 of the package 100 and the further contact section 60 of the counter member 50 can connect the inner space 120 of the package 100 and the inner space 54 of the counter member 50. In particular, the inner space 54 of the counter member 50 can be fluidically connected with the inner space 120 of the package 100, when the penetration device 40 penetrates the bottom side 114 and the further contact section 60.

In an embodiment, the penetration device 40, particularly the tapered element 41, forms a further through-opening 162 in the further joint sterile barrier 152, when penetrating the further joint sterile barrier 152.

In an embodiment, the pointed end 44 of the tapered element 41 can stick into the inner space 54 of the counter member 50.

In an embodiment, the penetration device 40, particularly the tapered element 41 penetrates the contact section 20, the top side 112 of the wall 110 of the package 100, the bottom side 114 of the wall 110 of the package 100 and the further contact section 60. This means that the penetration device 40 can penetrate the joint sterile barrier 150 and the further joint sterile barrier 152.

Penetrating the joint sterile barrier 150 and the further joint sterile barrier 152 can connect the inner space 14 of the container with the inner space 54 of the counter device 50 via the inner space 120 of the package 100. In particular, the inner space 14 of the container 10 can be fluidically connected with the inner space 54 of the counter member 50. In other words, penetrating the joint sterile barrier 150 and the further joint sterile barrier 152 can connect the inner space 120 of the package 100 with the inner space 14 of the container and the inner space 54 of the counter device 50.

According to an embodiment, in the penetration position, the mounting plate 48 of the penetration device 40 is positioned in the inner space 14 of the container 10. In the penetration position, the absorber 30 can be positioned in the inner space 14 of the container 10.

Figure 3:
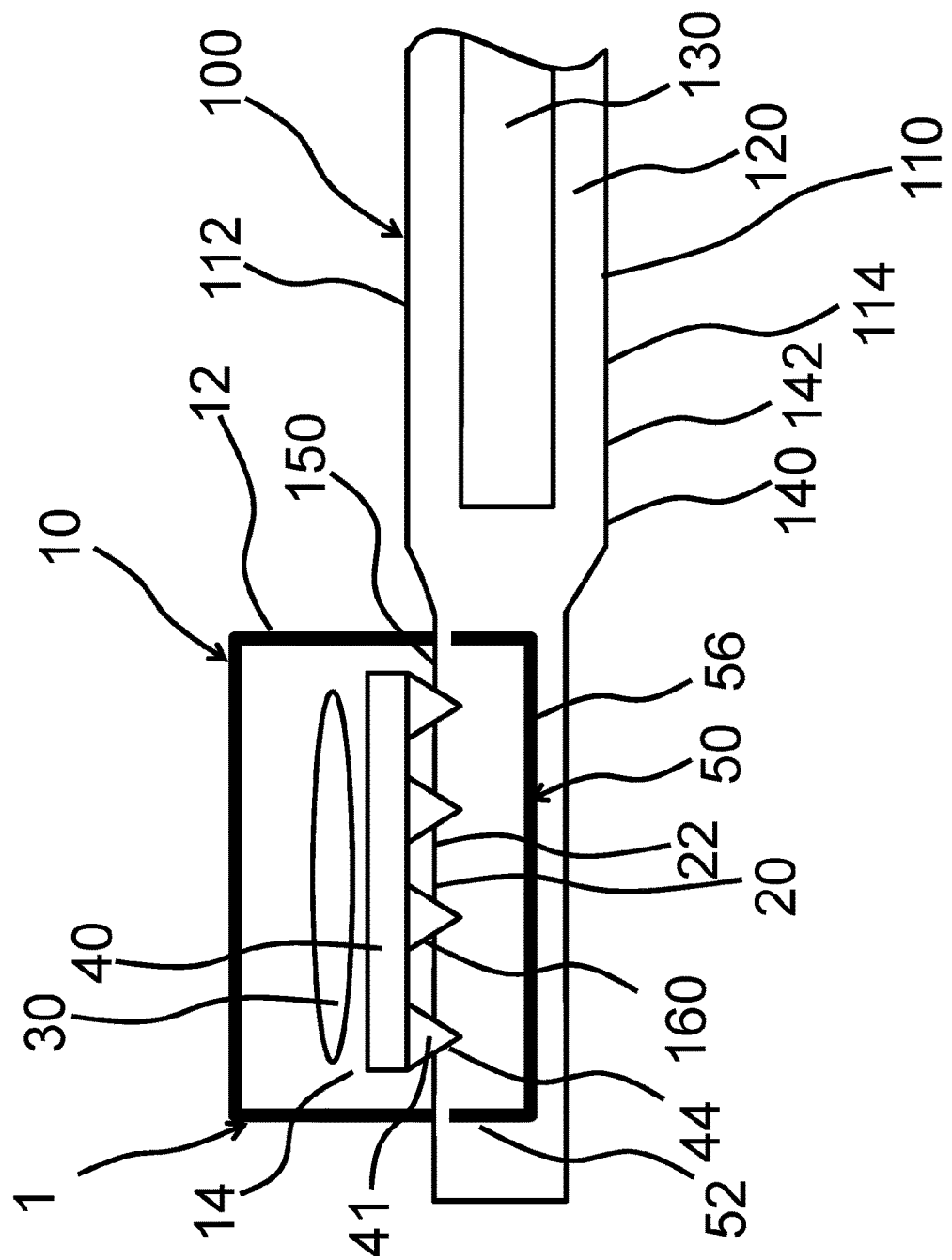
FIG. 3 shows a schematic cross section view of a counter member arranged in the inner space of the package.

FIG. 3 illustrates a further embodiment of an absorber device 1 according to the invention. The absorber device 1 can include a container 10 as described above. In particular, the container 10 can include a wall 12 including a contact section 20 which includes an outer surface 22. The wall 12 can delimit an inner space 14 of the container 10. According to an embodiment, the absorber device 1 further includes an absorber 30 and a penetration device 40, including at least one tapered element 41.

The package 100 can include the components as described above. In particular, the package 100 can include a wall 110 delimiting an inner space 120 of the package 100. An object 130 can be positioned in the inner space 120 of the package 100. The wall 110 of the package 100 can include a top side 112 and an opposing bottom side 114. The wall 110 of the package 100 can include an outer surface 140 and an inner surface 142.

In the embodiment presented in FIG. 3, a counter member 50 is positioned in the inner space 120 of the package 100.

The counter member 50 can include a wall 52 of the counter member 50. In particular, the counter member 50 can include a back wall 56 of the counter member 50. The back wall 56 of the counter member 50 can extend parallel to the bottom side 114 of the wall 110 of the package 100. The back wall 56 of the counter member 50 can extend parallel to the top side 112 of the wall 110 of the package 100.

The outer surface 22 of the contact section 20 can contact the wall 110 of the package 100, particularly the top side 112 of the wall 110 of the package 100. The outer surface 22 of the contact section 20 can be positively connected with the wall 110 of the package 100. The outer surface 22 of the contact section 20 can connected with the outer surface 140 of the wall 110 of the package 100. In an embodiment, the outer surface 22 of the contact section 20 is adhesive such that the outer surface 22 of the contact section 20 can adhere to the wall 110 of the package 100. When the outer surface 22 of the contact section 20 is positively connected with the wall 110 of the package 100, they can form a joint sterile barrier 150.

The container 10 can contact the outer surface 140 of the wall 110 of the package 100. In an embodiment, the counter member 50 can contact the inner surface 142 of the wall 110 of the package 100. When clamping the package 100 between the container 10 and the counter member 50, the wall 110 of the package can be clamped between the container 10 and the counter member 50.

The container 10 can be arranged such with respect to the wall 110 of the package 100 that the container 10 faces the counter member 50.

In FIG. 3, a penetration position is illustrated. In the penetration position, the penetration device 40 can penetrate the contact section 20. In the penetration position, the penetration device 40 can penetrate the wall 110 of the package 100, particularly the top side 112 of the wall 110. The penetration device 40 can penetrate the joint sterile barrier 150. According to an embodiment, the tapered element 41 can penetrate the joint sterile barrier 150. This means that the penetration device 40 can insert a through-opening 160 in the joint sterile barrier 150. The pointed end 44 of the tapered element 41 can stick into the inner space 120 of the package 100. Via the through-opening 160, the inner space 14 of the container 10 can be connected, particularly fluidically connected, with the inner space 120 of the package 100.

Figure 4:
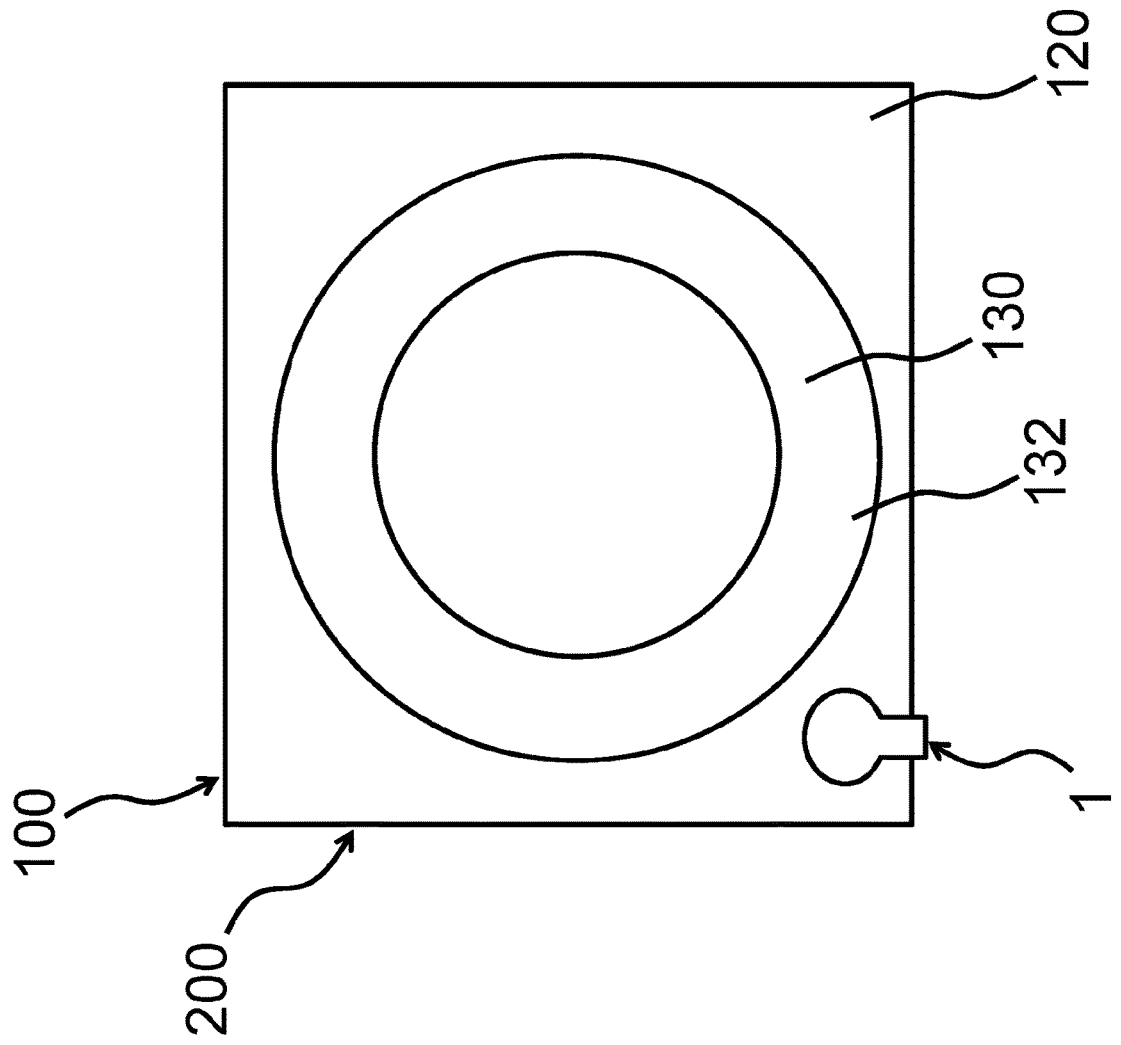
FIG. 4 illustrates a packaging system according to the invention, wherein a medical device is positioned in the package and the absorber device is arranged on the package.

FIG. 4 shows a schematic top view of an embodiment of a package 100 and an embodiment of an absorber device 1, wherein the absorber device 1 is arranged on the package 100. FIG. 4 shows an embodiment of a packaging system 200.

An object 130, particularly a medical device 132 can be arranged in the inner space 120 of the package 100. The medical device 132 can be a dispenser ring with catheter. The absorber device 1 can be arranged on the package 100.

The invention claimed is:

1. An absorber device for absorbing a fluid enclosed by a package, comprising:
a container having a wall enclosing a container inner space, the wall comprising a container contact section that is configured to be penetrated,
an absorber arranged in the container inner space, and
a movable penetration device configured to be moved from a first position to a second position, wherein in the first position, the penetration device is positioned in the container inner space and in the second position is positioned to penetrate the contact section and extend beyond the container contact section such that a package arranged against the container contact section can be penetrated and have its inner space fluidically connected to the absorber in the container inner space, and
a counter member having a counter contact section facing the container contact section, wherein the container and the counter member are configured to be movable towards each other to clamp a portion of a package arranged therebetween.

2. The absorber device according to claim 1, wherein the container contact section comprises an outer surface configured to connect to a package arranged against the container contact section.

3. The absorber device according to claim 1, wherein the container contact section comprises or consists of aluminium or an aluminium alloy.

4. The absorber device according to claim 1, wherein the penetration device comprises at least one tapered element.

5. The absorber device according claim 1, wherein the absorber comprises an oxygen absorber.

6. The absorber device according to claim 1, wherein the container inner space is sterile.

7. The absorber device according to claim 1, wherein the counter contact section is configured to be penetrated.

8. The absorber device according to claim 1, wherein the counter contact section comprises an adhesive outer surface.

9. The absorber device according to claim 1, wherein the counter contact section is arranged distant to the container contact section in the first position to permit positioning of a portion of package between the counter contact section and the container contact section.

10. The absorber device according to claim 1, wherein the penetration device penetrates the counter contact section in the second position.

11. The absorber device according to claim 1, wherein the container and the counter member are connected to one another.

12. The absorber device according to claim 1, wherein the contact section comprises a foil comprising or consisting of aluminium or an aluminium alloy.

13. The absorber device according to claim 1, wherein the absorber comprises a moisture absorber.

14. A packaging system for an object to be sterilised, comprising the absorber device of claim 1 and a package comprising a portion configured to be positioned against the container contact section.

15. The packaging system according to claim 14, wherein the package comprises a counter member arranged in the package inner space, wherein the counter member and the container are arranged and configured such that the container is movable towards the counter member to clamp the portion of the package between the container and the counter member.

16. A method to absorb a fluid residing in an inner space of a package, using the absorber device of claim 1, comprising the steps of:
arranging the package and the absorber device with respect to each other such that the container contact section is arranged on an outer surface of a wall of the package,
moving the penetration device from the first position to the second position such that the penetration device penetrates the container contact section and the wall of the package to thereby allow the fluid to pass from the package inner space the container inner space to be absorbed by the absorber.

* * * * *